US00PP11223P

United States Patent [19]

Marciel et al.

[11] Patent Number: Plant 11,223

[45] Date of Patent: Feb. 15, 2000

[54] FLORIBUNDA ROSE PLANT NAMED 'DEVRUDI'

[75] Inventors: Stanley G. Marciel; Jeanne A. Marciel, both of Aptos, Calif.

[73] Assignee: DeVor Nurseries, Inc., Watsonville, Calif.

[21] Appl. No.: 08/944,069

[22] Filed: Oct. 2, 1997

[51] Int. Cl.[7] ..... A01H 5/00

[52] U.S. Cl. ..... Plt./149

[58] Field of Search ..... Plt./22, 26, 27, Plt./28, 141, 148, 149, 150, 102, 107

*Primary Examiner*—Howard J. Locker
*Attorney, Agent, or Firm*—Christie, Parker & Hale, LLP

[57] ABSTRACT

A floribunda rose plant variety producing single deep pink to light red flowers in clusters.

1 Drawing Sheet

BACKGROUND OF THE INVENTION

The present invention relates to a new and distinct floribunda rose variety which was originated by my crossing as seed and pollen parents unnamed, unpatented and undistributed seedlings. The varietal denomination of this new rose is 'Devrudi'.

SUMMARY OF THE INVENTION

Among the novel characteristics possessed by the new variety which distinguish it from its parents and all other varieties of which I am aware are its attractive, single, deep pink to light red flowers that bloom throughout the growing season on a vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction may be also used.

COMPARISON WITH PARENTS

The seed parent produces deep white flowers, whereas the new variety 'Devrudi' produces deep pink to light red flowers. The pollen parent plant is smaller and not as vigorous.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent*.—Unnamed, unpatented seedling.

*Pollen parent*.—Unnamed, unpatented seedling.

Class: Floribunda.

The following is a detailed description of the new variety, from specimens grown in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:

(1) *Size*.—Small, about 1.8 cm to 2.2 cm long and about 0.5 cm wide.

(2) *Form*.—Pointed.

(3) *Color*.—When sepals first divide, bud color is near 47A to 52A.

(4) *Sepals*.—Longer than green bud, sepals spread and become horizontal when bloom opens and ages; some sepals are foliaceous with leaf-like protrusions, about 1.8 to 2.2 cm. Color: Near 144A with tinges of near 146C on sides.

(5) *Pedicel*.—Length: About 3 to 4.5 cm. Aspect: Rough. Strength: Thin, erect. Color: Near 144B.

(6) *Bracts*.—Usually 1 to 2 per pedicel, near 148B, acute-elliptical with acuminate apex about 1.8 to 2.2 cm. below calyx.

B. Bloom:

(1) *Size*.—Average size when fully expanded about 8.5 cm. to 10 cm.

(2) *Borne*.—Clusters of about 3 to 14 blooms.

(3) *Form*.—Single, informal.

(4) *Petalage*.—Number of petals under normal conditions — about 5 to 6.

(5) *Color*.—Top surface near 54B to 55D under surface near 54A with near 55C at tip. Base of petals — Near 150D. General tonality from a distance: Pink.

(6) *Color change*.—Color changes to a paler shade of pink. Petal top surface: Near 55C. Petal under surface: Near 55B at tip; near 55C in middle and near 56A at base. General tonality at a distance: Pink.

Petals:

(1) *Texture*.—Thick, smooth.

(2) *Appearance*.—Matte inside and outside (3) *Form*.—Elliptical, broad with rounded edge.

(4) *Arrangement*.—Single.

(5) *Petaloids*.—Few, 1 to 2.

(6) *Fragrance*.—Slightly fruity.

(7) *Lasting quality*.—On plant about 10 to 12 days, after cutting about 4 to 6 days.

(8) *Persistence*.—Petals drop off cleanly.

REPRODUCTIVE ORGANS

A. Stamens:

(1) *Arrangement*.—Irregularly arranged around styles.

(2) *Anthers*.—Near 181B.

(3) *Filaments*.—Near 181C at top with near 11A toward base.
(4) *Pollen*.—Near 23B.

B. Pistils:
(1) *Styles*.—Bunched, even.
(2) *Stigmas*.—Near 12D.

C. Characteristics of hips: Globose; about 1.5 cm. wide, about 1.5 cm. long; near 31A when mature.

PLANT

A. Form: Upright, compact.

B. Growth: Very vigorous; about 80 cm. to about 120 cm. in height and about 70 to 80 cm. in width at first season.

C. Foliage: Compound 3, 5 and 7 leaflets.
(1) *Size*.—Medium.
(2) *Quantity*.—Abundant.
(3) *Color*.—New foliage near 147A; under side near 146B mature foliage upper side near 147A, under side near 146B.
(4) *Shape*.—Oval.
(5) *Texture*.—Upper side semi-leathery; under side leathery.
(6) *Edge*.—Serrated.
(7) *Serration*.—Denticulate.
(9) *Stipules*.—Adnate, parallel auricle facing outwards with bearded margins.
(10) *Rachis*.—Smooth.
(11) *Petioles*.—Top near 144B, under side near 145A.
(12) *Auricle*.—Short, narrow, facing outwardly, slightly bearded margins.
(13) *Resistance to disease*.—Very resistant to blackspot, mildew and rust.

D. Wood:
(1) *New wood*.—Color near 143C, bark smooth, many thorns.
(2) *Old wood*.—Color near 144A, bark smooth, many thorns.

E. Flower Stem: About 8 to 20 cm. from last cut.

F. Thorns:
(1) *Thorns*.—Quantity: On main stalk, profuse; laterals from stalk, profuse. Form: Straight, thin. Length: About 0.05 to 0.07 cm. Color: Near 165A. Position: Irregular.
(2) *Prickles*.—None.

G. Winter hardiness: Winter hardy in Watsonville, Calif.

We claim:

1. A new and distinct floribunda rose plant of the variety, substantially as shown and described.

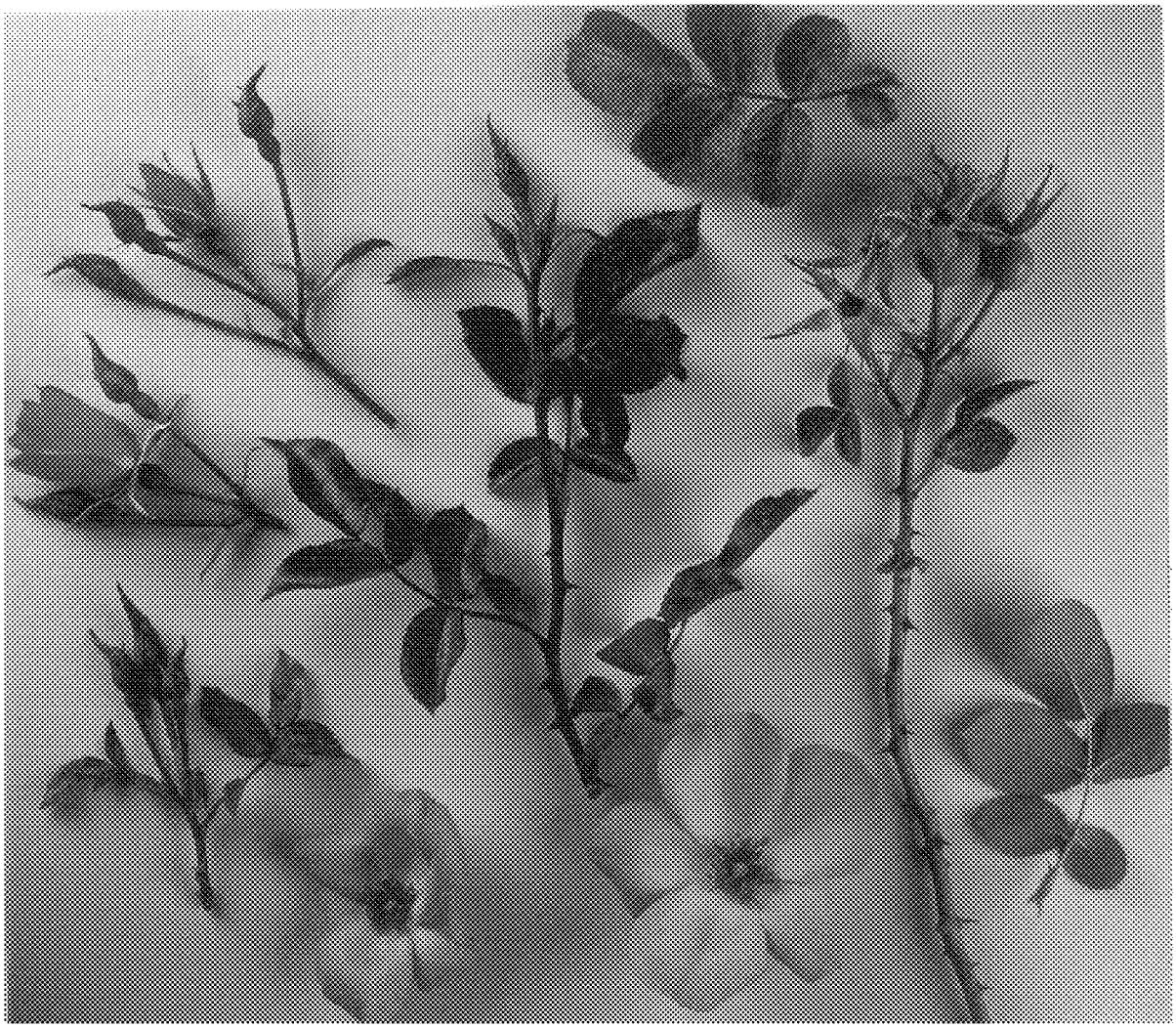

* * * * *